(12) United States Patent
Vakharia et al.

(10) Patent No.: US 8,317,827 B2
(45) Date of Patent: Nov. 27, 2012

(54) SUTURING DEVICES AND METHODS

(75) Inventors: Omar J. Vakharia, Cincinnati, OH (US); Andrew M. Zwolinski, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 597 days.

(21) Appl. No.: 12/349,942

(22) Filed: Jan. 7, 2009

(65) Prior Publication Data

US 2010/0174296 A1 Jul. 8, 2010

(51) Int. Cl.
*A61B 17/04* (2006.01)
(52) U.S. Cl. ......................... 606/232; 606/139
(58) Field of Classification Search ........... 606/139, 606/232, 144, 151
See application file for complete search history.

(56) References Cited

U.S. PATENT DOCUMENTS

| | | | |
|---|---|---|---|
| 5,234,445 A | 8/1993 | Walker et al. | |
| 5,282,809 A | 2/1994 | Kammerer et al. | |
| 5,330,491 A | 7/1994 | Walker et al. | |
| 5,466,241 A | 11/1995 | Leroy et al. | |
| 5,501,690 A | 3/1996 | Mesamer et al. | |
| 5,693,059 A * | 12/1997 | Yoon | 606/139 |
| 5,899,921 A * | 5/1999 | Caspari et al. | 606/232 |
| 6,221,084 B1 | 4/2001 | Fleenor | |
| 6,221,107 B1 * | 4/2001 | Steiner et al. | 623/13.14 |
| 6,695,852 B2 | 2/2004 | Gleason | |
| 2006/0259043 A1 | 11/2006 | Miyamoto | |
| 2006/0259044 A1 * | 11/2006 | Onuki et al. | 606/139 |
| 2007/0213587 A1 | 9/2007 | Moon | |
| 2007/0255317 A1 * | 11/2007 | Fanton et al. | 606/232 |
| 2007/0270907 A1 | 11/2007 | Stokes | |
| 2007/0270908 A1 | 11/2007 | Stokes | |

OTHER PUBLICATIONS

International Search Report, from PCT/US10/20202, mailed Aug. 19, 2010.
International Search Report and Written Opinion for Application No. PCT/US10/20202, dated Aug. 19, 2010 (15 pages).

* cited by examiner

*Primary Examiner* — Corrine M McDermott
*Assistant Examiner* — Gregory Anderson

(57) ABSTRACT

Methods and devices are provided for delivering a preloaded loop of suture extending from a knotting element to tissue to be ligated within a body. The knotting element can be threaded with a loop of suture and loaded onto a deployment device using a loading device. A protective sheath can be placed around the knotting element and the loop of suture to facilitate safe insertion of the loop of suture through a working channel of a minimally invasive device.

28 Claims, 10 Drawing Sheets

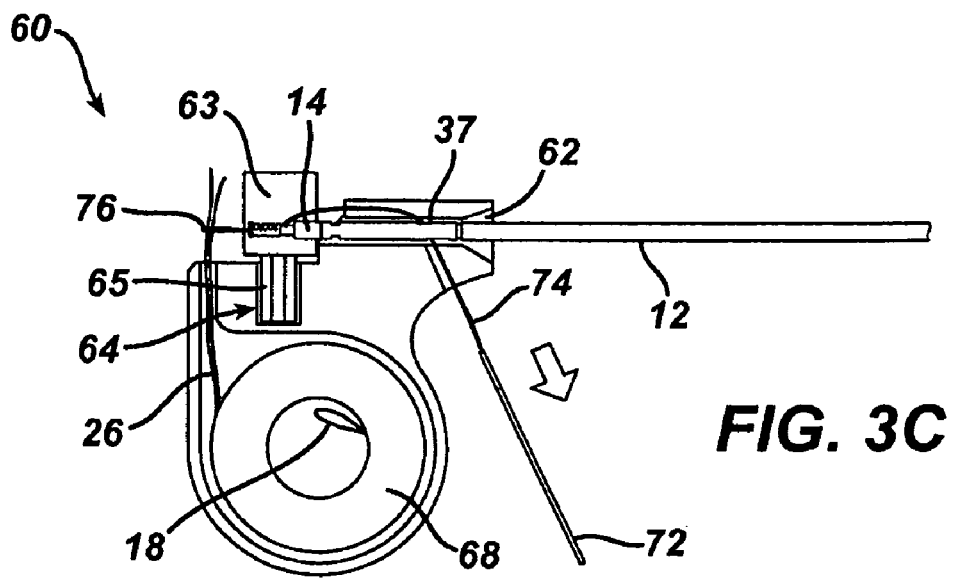
FIG. 3C
FIG. 3D
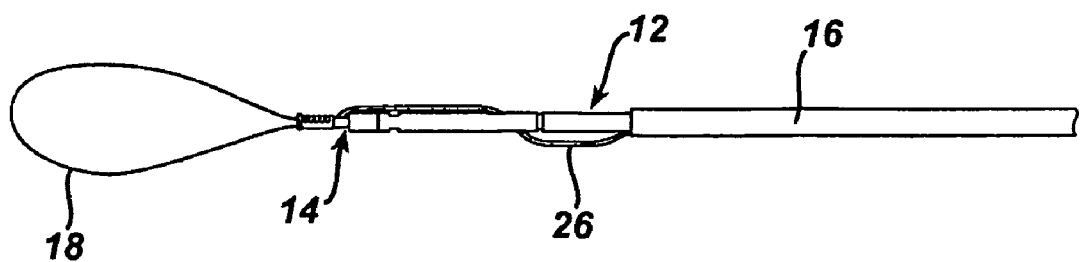

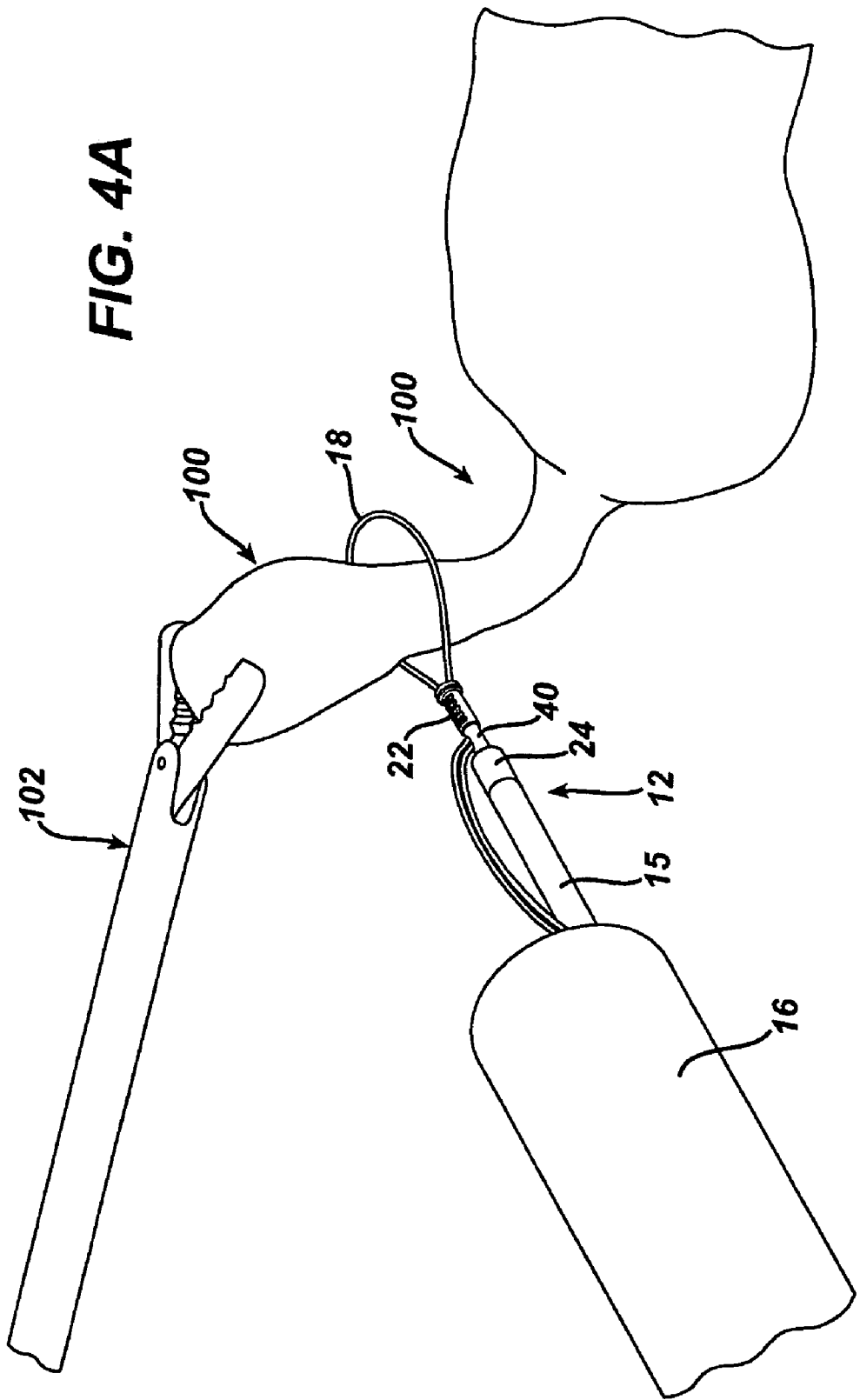

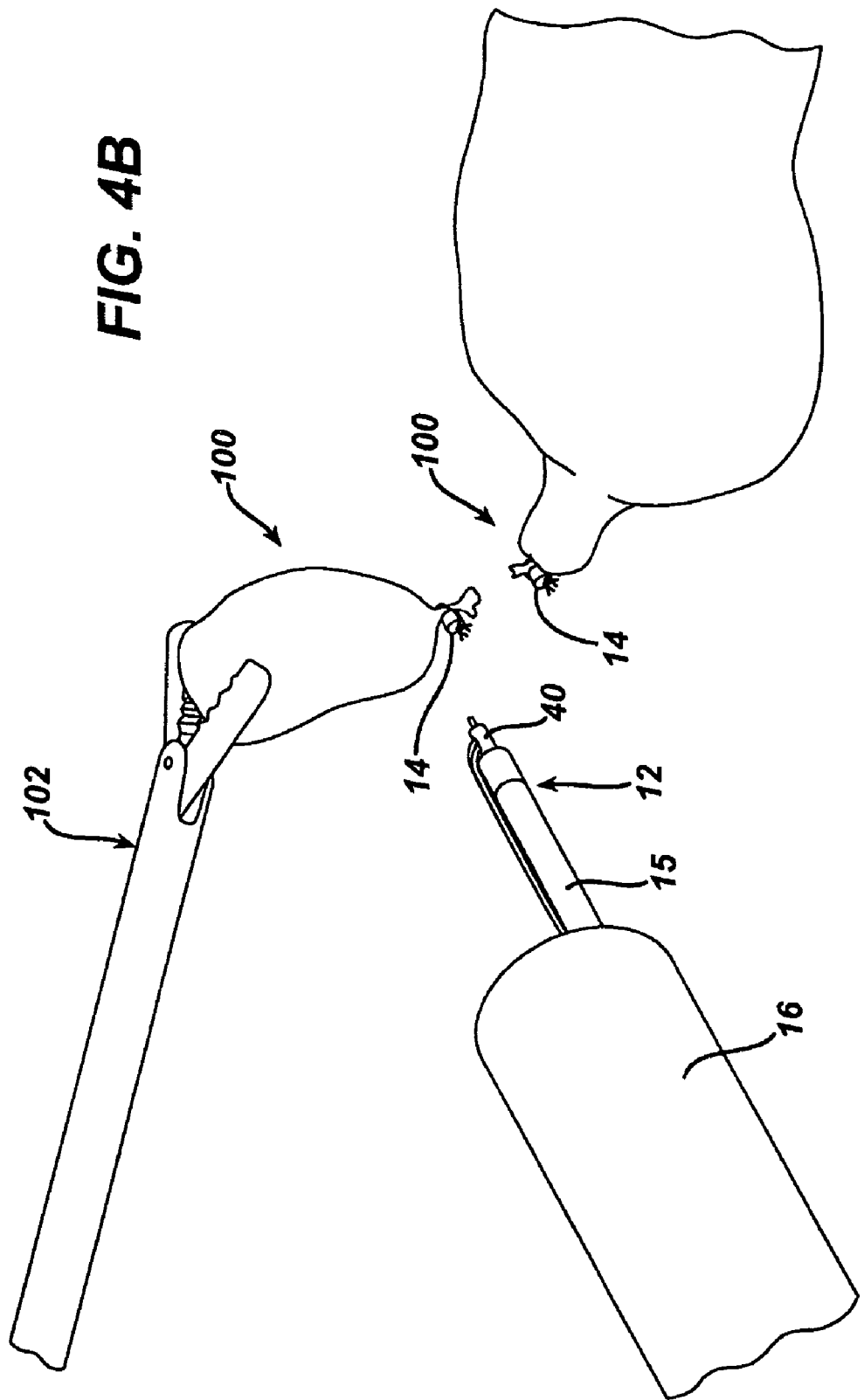

SUTURING DEVICES AND METHODS

FIELD OF THE INVENTION

The present invention relates to methods and devices for endoscopic surgical procedures for tissue ligation.

BACKGROUND OF THE INVENTION

In many surgical procedures, suturing and ligating are required to close wounds. For example, suturing to approximate tissue, which requires the formation of a suture knot for placement of a stitch, is often required for proper healing of lacerations and surgical incisions. Additionally, ligating blood vessels or other tubular organs to be cut within the surgical site is often necessary in numerous surgical procedures. The primary reason for ligating the vessels and/or tubular organs is to maintain the surgical site free of an excess of blood and to reduce blood loss in the patient.

Conventionally, surgeons have performed ligations using ligatures, which are long, relatively straight strands of suture material. The ligature can be secured by forming a suture knot to place a stitch or a knotting element can be threaded onto the ligature after the ligature is looped around the vessel or organs desired to be closed. Unfortunately, forming a knot or threading a knotting element using conventional ligatures is tedious and time-consuming during surgical applications where a surgeon's manual operative techniques within the surgical site are severely restricted.

Thus, there is a need for improved suturing methods and devices.

SUMMARY OF THE INVENTION

The present invention provides various methods and devices for suturing tissue. In one embodiment, a tissue ligation system is provided and can include a deployment device having a knotting element coupled thereto, a strand of suture passed through the knotting element to form a loop extending from the knotting element, and a sheath slidably disposed over the deployment device, the knotting element, and the loop. The loop can extend from a distal end of the knotting element and the deployment device can be coupled to a proximal end of the knotting element. In some embodiments, a size of the loop extending from the knotting element can be adjustable relative to the knotting element. For example, the size of the loop can be increaseable. In other embodiments, the loop can be bendable out of a plane containing the loop to reorient the loop to better receive tissue therethrough. The loop can generally be configured to be placed around tissue and tightened to ligate tissue.

In one exemplary embodiment, the knotting element can include an inner member and an outer member slidably movable relative to the inner member. The inner member and the outer member can be moveable between an open configuration in which the strand of suture is freely adjustable relative to the knotting element, and a locked configuration in which the inner and outer members engage the strand of suture therebetween. In some embodiments, the inner and outer members are positioned substantially concentrically to grip the strand of suture in the locked configuration. The deployment device can be configured to move the knotting element to the locked position. While the sheath can have many configurations, in one embodiment, the sheath can be configured to protect the loop of suture during delivery through tissue. In addition, the sheath can be retractable from around the loop of suture.

Methods for deploying a suture locking device are also provided and can include positioning a knotting element and a loop of suture extending from the knotting element in a delivery sheath, inserting the delivery sheath through tissue, e.g., through the delivery sheath being inserted through a working channel of a minimally invasive device, and retracting the delivery sheath from around the loop of suture. Methods can further include positioning the loop of suture around tissue to be ligated and deploying the knotting element to engage the loop of suture. In some embodiments, positioning the loop of suture can include manipulating the loop of suture to position the loop of suture around tissue. In other embodiments, tissue to be ligated can be pulled through the loop of suture and the knotting element can be deployed to engage the loop of suture.

In one exemplary embodiment, positioning the knotting element can include advancing the delivery sheath over a deployment device having the knotting element coupled to a distal end thereof. Prior to positioning, the suture can be threaded through the knotting element and the knotting element loaded onto the deployment device using a loading device. In other embodiments, the deployment device can be activated to deploy the knotting element to engage the suture. Prior to activating, the knotting element can be advanced along the suture to engage tissue with the loop of suture. The knotting element can be released from the deployment device and a second knotting element can be reloaded with a suture loop extending therefrom onto the deployment device using the loading device.

In one exemplary method, the size of the loop of suture can be increased. The method can also include bending the loop of suture out of a plane containing the loop of suture to better orient the loop of suture to receive tissue therethrough.

In other aspects, a loading device is provided and can include a housing having a suture loading portion for loading a loop of suture into a knotting element, and a knot loading portion for loading the knotting element onto a delivery device for delivering the knotting element and the loop of suture through tissue. The suture loading portion can include a single thread of suture and a suture loading wheel. The knot loading portion can include a port for receiving the delivery device to be loaded with the knotting element loaded with a loop of suture.

In another aspect, a kit is provided and can include a loading device having a knotting element disposed therein and a strand of suture disposed therein configured to be threaded through the knotting element. A delivery device can also be included and can be configured to receive the knotting element with suture threaded therethrough and to deliver the knotting element and suture through tissue. The delivery device can include a deployment device for deploying the knotting element to engage the suture, and a sheath disposed over the deployment device.

BRIEF DESCRIPTION OF THE DRAWINGS

The invention will be more fully understood from the following detailed description taken in conjunction with the accompanying drawings, in which:

FIG. 3C is a cross-sectional view of the loading device of FIG. 3A illustrating threading of a knotting element;

FIG. 3D is a side view of a threaded knotting element loaded onto the deployment device of FIG. 3B;

FIG. 4A is a perspective view of the embodiment of FIG. 1A with the loop positioned around tissue to be ligated;

FIG. 4B is a perspective view of the embodiment of FIG. 1A with the knotting element deployed to cause the loop to ligate tissue;

DETAILED DESCRIPTION OF THE INVENTION

Figure 1A:
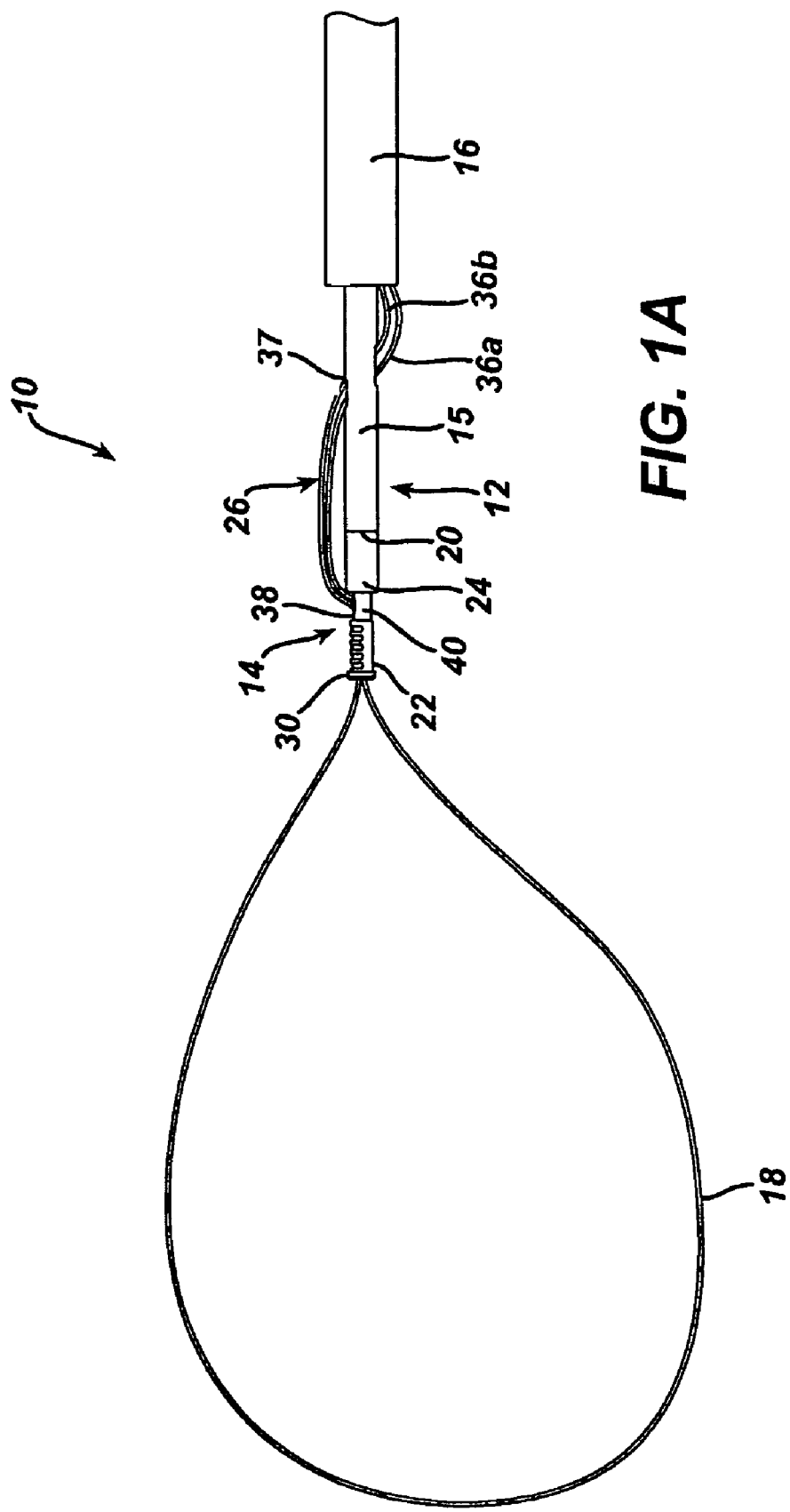
FIG. 1A is a side view of one embodiment of a suture locking device having a knotting element disposed thereon and having a loop of suture extending therefrom.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides methods and devices directed to delivering a suture locking device and a loop of suture into a body cavity to ligate tissue within the cavity. In certain embodiments, a deployment device can be loaded with a knotting element having a preloaded loop of suture extending therefrom. A protective sheath can be disposed around the deployment device, the knotting element, and the loop of suture to protect the same during delivery through tissue and into a body cavity. Once within proximity to tissue to be ligated, the sheath can be retracted from around the loop of suture and optionally around the knotting element to allow the loop of suture to engage and ligate tissue. The knotting element can be deployed to lock the suture relative to the tissue. In this way, a surgeon or operator is spared the difficulties that can arise from having to thread a knotting element onto a suture after the suture is positioned to ligate tissue.

In one exemplary embodiment shown in FIGS. 1A-1D, a delivery device 10 is provided and can generally include a deployment device 12 extending from a handle 19, a knotting element 14 having a loop of suture 18, and a delivery sheath 16. The knotting element 14 can generally be positioned at a distal end 20 of the deployment device 12, and the delivery sheath 16 can be slidably disposed around one or all of the loop of suture 18, the deployment device 12, and the knotting element 14 as will be described in detail below. The delivery sheath 16 can protect the loop of suture 18 during delivery of the loop of suture 18 to a body cavity. The loop of suture 18 can be positioned around tissue and tensioned to engage tissue positioned through the loop of suture 18. The handle 19 can be positioned at a proximal end of the delivery device 10 and can control activation of the deployment device 12 through movement of an actuator shaft 15. Activation of the handle 19 or using another activation mechanism known in the art can generally cause the deployment device 12 to deploy and optionally release the knotting element 14 from the distal end 20 thereof to engage the loop of suture 18, thereby locking the loop of suture 18 around tissue. In one exemplary embodiment, a loading device can be used to thread a strand of suture through the knotting element 14 and to load the knotting element 14 onto the deployment device 12.

While the delivery device 10 can be used as needed in any surgical procedures now known or yet to be developed, in one embodiment, the delivery device 10 can be used in minimally invasive, laparoscopic, or endoscopic procedures. The delivery device 10 can be inserted through an endoscope, trocar cannula, etc. or any other pathway into a body cavity. The knotting element 14 having the preformed loop of suture 18 extending therefrom is particularly advantageous for use in minimally invasive procedures as the surgical space and ease of maneuverability are often limited. Unlike prior art knotting elements which require that a loop of suture be threaded through the knotting element after the suture is positioned around tissue, embodiments of the present invention provide a loop of suture that is ready to be applied to tissue as soon as the deployment device is inserted to the desired location within a body. The loop of suture 18 and the knotting element 14 can generally be used to ligate any tissue within the human body including, but not limited to, ovaries, blood vessels, fallopian tubes, cystic bundles, large pedunculated colorectal polyps, polypoid AVMs, adjunct to clip hemostasis, colonic lipoma, lymphangioma, colonic and esophageal fistula, etc. The loop of suture 18 and the knotting element 14 can also be used to perform retrieval procedures, such as, for example, the retrieval of self-expanding metal stents.

While the deployment device 12 can have many configurations, it can generally be configured to deploy the knotting element 14 to engage the loop of suture 18 and secure it around tissue. As shown in FIGS. 1A-1D, in some embodiments, the knotting element 14 can be positionable on the distal end 20 of the deployment device 12 and it can be configured to be deployed therefrom through the use of the handle 19 or other activation mechanism. The handle 19 can include a trigger 25 coupled to the actuator shaft 15 such that by squeezing the trigger 25, or using some other activation mechanism, the actuator shaft 15 can deploy the knotting element 14 by slidably moving an outer member 24 of the knotting element 14 over an inner member 22 of the knotting element 14 such that the strand of suture 26 is engaged therebetween. The deployment device 12 can simultaneously or subsequently release the knotting element 14 from the distal end 20 thereof to lock the strand of suture 26 such that the loop of suture 18 is secured around tissue.

There are many ways in which the knotting element 14 can be connected to and/or within the deployment device 12. In the illustrated embodiment, the inner member 22 of the knotting element 18 has an extension portion 40 extending proximally from its proximal end. The elongate, hollow actuator shaft 15 can have an inner shaft (not shown) that engages the inner member 22 such that the distal-most end of the actuator shaft 15 is flush with and/or adjacent to a proximal-most end of the outer member 24. The inner shaft can have grooves, tabs, internal surface features, or any other engagement mechanism configured to engage the extension portion 40, while allowing the actuator shaft 15 to slidably move over the extension portion 40 upon activation of the deployment device 12. Activation of the trigger 25 can be effective to cause the actuator shaft 15 to move relative to the inner shaft to thereby move the outer member 24 over the inner member 22. Once the knotting element 14 is locked such that the outer member 24 is enclosing the inner member 22 with the strand of suture 26 secured therebetween, further distal movement of the actuator shaft 15 relative to the inner shaft can cause a frangible portion (now shown) formed on the extension portion 40 to be snapped or broken thereby releasing the knotting element 14. As will be appreciated by those skilled in the art, the deployment device 12 can have many configurations for retaining and deploying the knotting element 14 therefrom. A detailed description of the structure and action associated with one exemplary deployment device and trigger mechanism can be found in U.S. Patent Application No. 2007/0270907 entitled "Suture Locking Device," filed May 19, 2006 and incorporated herein by reference in its entirety.

As noted above, the delivery device 10 can also include the delivery sheath 16. The delivery sheath 16 is generally intended to provide protection for the loop of suture 18 as it is inserted into a patient's body through, for example, a working channel of a minimally invasive device. The delivery sheath 16 can have any shape known in the art, but preferably has a lumen in which to receive the loop of suture 18. In one embodiment, the delivery sheath 16 can be cylindrical or tubular in shape having a diameter and length sufficient to surround and enclose at least the loop of suture 18. The delivery sheath 16 can be slidably movable relative to the deployment device 12 such that it can be moved from a configuration in which it extends distally beyond the knotting element 14 to concentrically surround the loop of suture 18, and a configuration in which it is positioned proximally to at least the loop of suture 18 so that the same can be positioned around tissue. The delivery sheath 16 can have any length as needed and in some embodiments, the delivery sheath 16 can have a length sufficient to surround the loop of suture 18 only. In other embodiments, the delivery sheath 16 can surround the knotting element 14 and optionally a portion of the deployment device 12 or the entire length of the deployment device 12, as shown.

The delivery sheath 16 can be extended and retracted by any methods known in the art. In some embodiments, the surgeon or other user can manually extend and retract the delivery sheath 16 during a procedure. For example, a sliding mechanism or button can be included on the handle housing 23 of the trigger assembly 19 and it can be in communication with the proximal end of delivery sheath 16 such that movement of the button or sliding mechanism is effective to cause the delivery sheath 16 to extend or retract. In the illustrated embodiment, the proximal end of the sheath is enlarged to form a handle that can be grasped and slit by user. In other embodiments, the delivery sheath 16 can be integrated with an activation mechanism and/or the trigger assembly 19 of the delivery device 10 such that it can be extended or retracted mechanically and/or electrically. For example, initial pressure applied to the trigger handle 25 could cause the delivery sheath 16 to retract from around the loop of suture 18 for positioning of the loop 18, while further applied pressure can deploy the knotting element 14 to engage and lock the strand of suture 26. A person skilled in the art will appreciate the various ways possible for extending and retracting the delivery sheath 16.

Figure 1B:
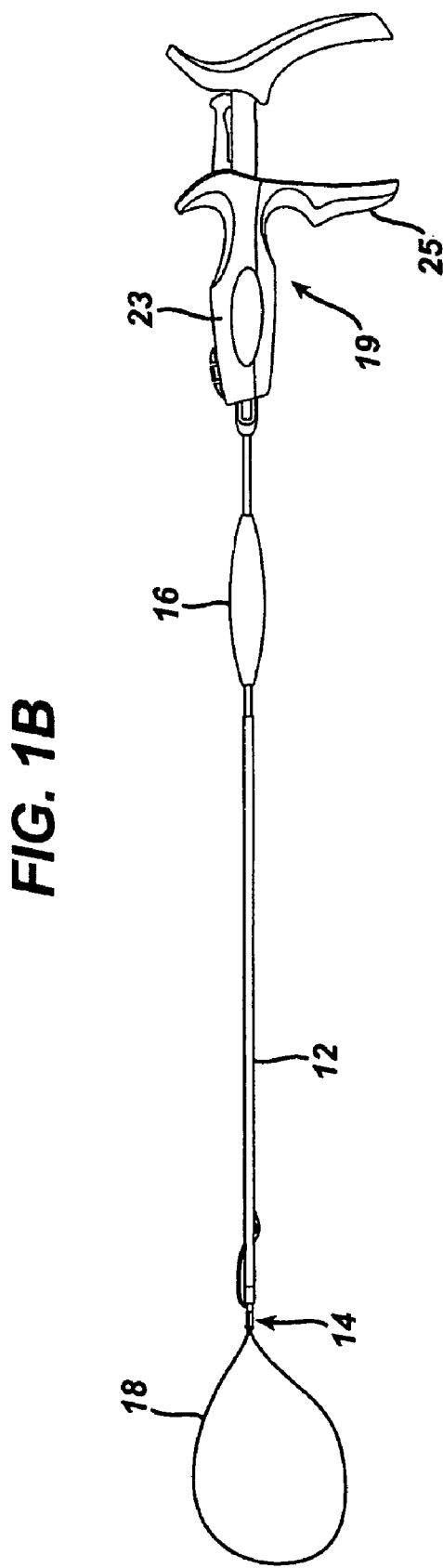
FIG. 1B is a side view of the embodiment of FIG. 1A showing an exemplary trigger assembly.
Figure 1C:
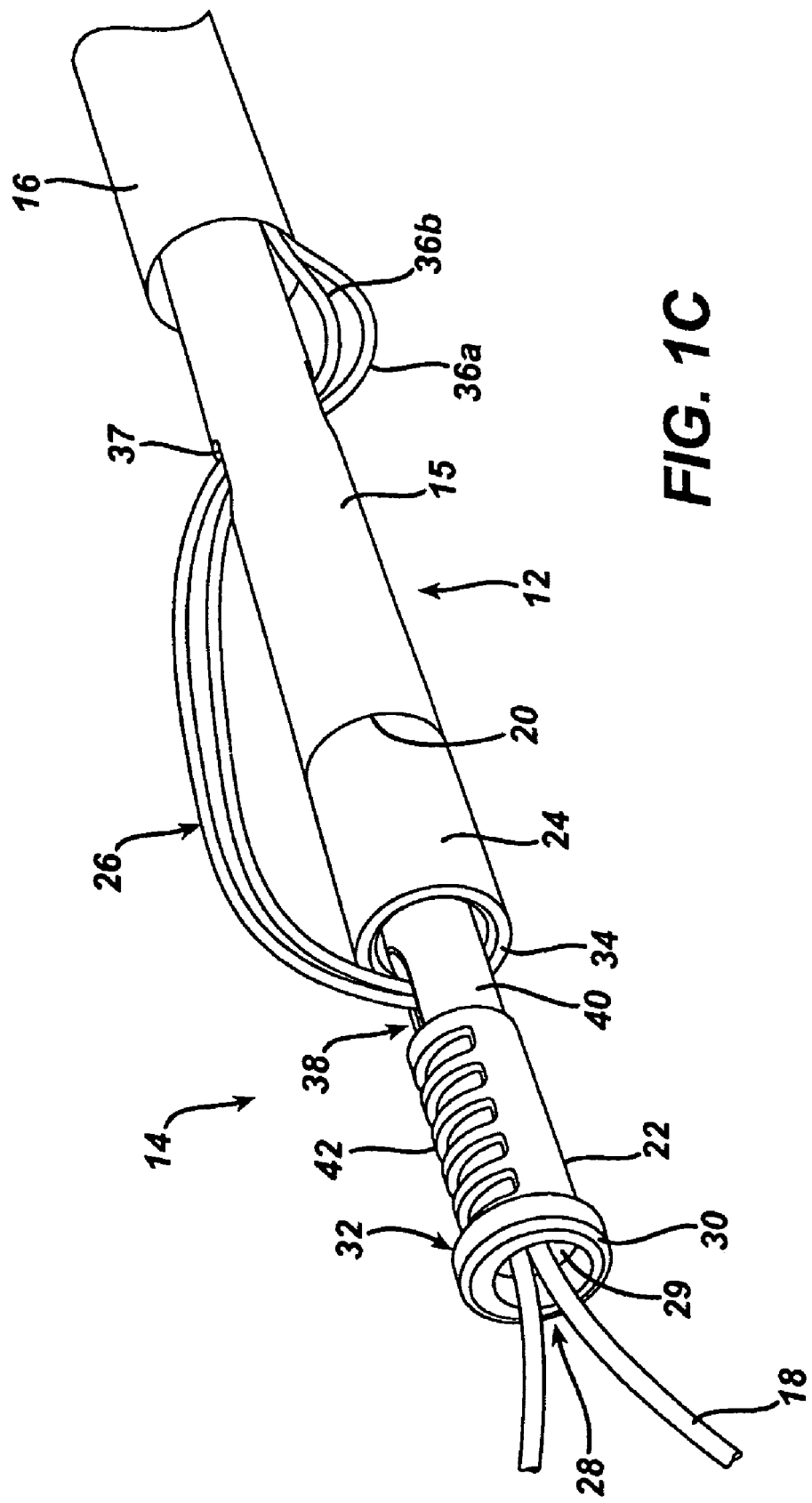
FIG. 1C is a perspective view of the embodiment of FIG. 1A with the knotting element in an open configuration.
Figure 1D:
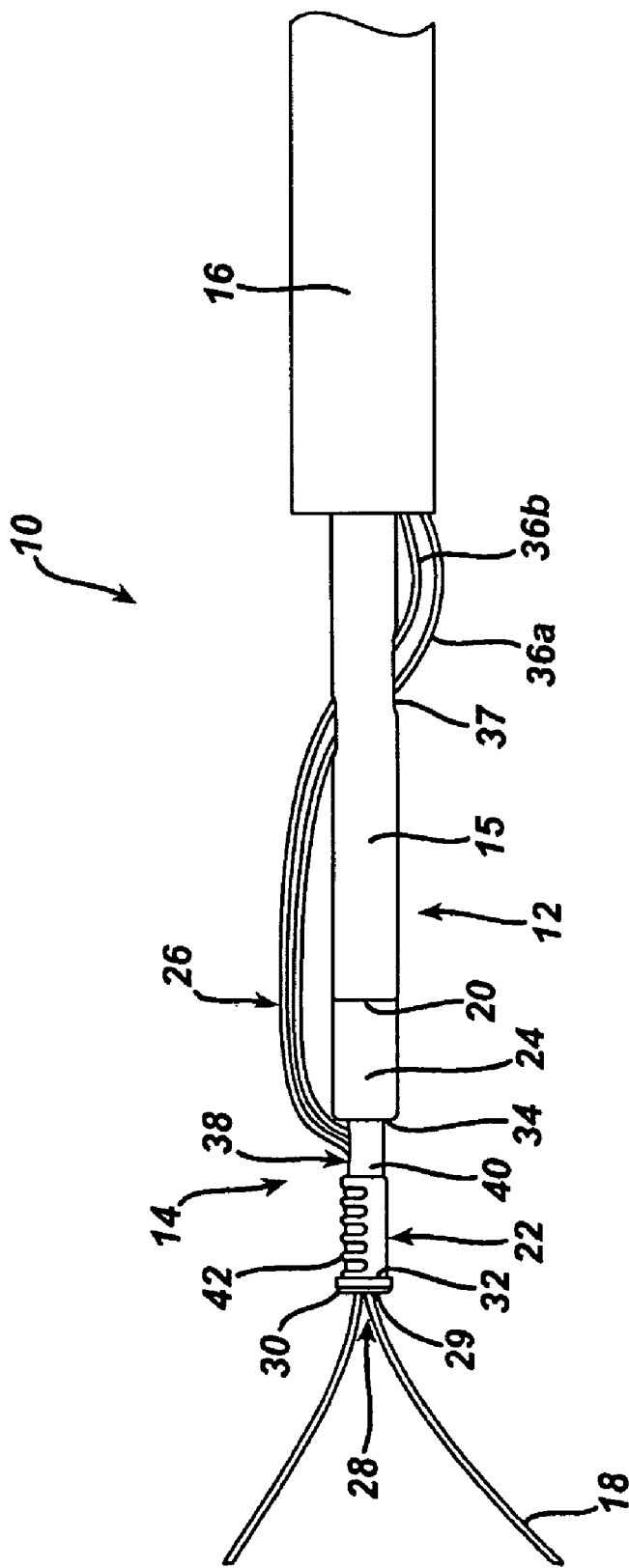
FIG. 1D is another side view of the embodiment of FIG. 1A with the knotting element in an open configuration.
Figure 2:
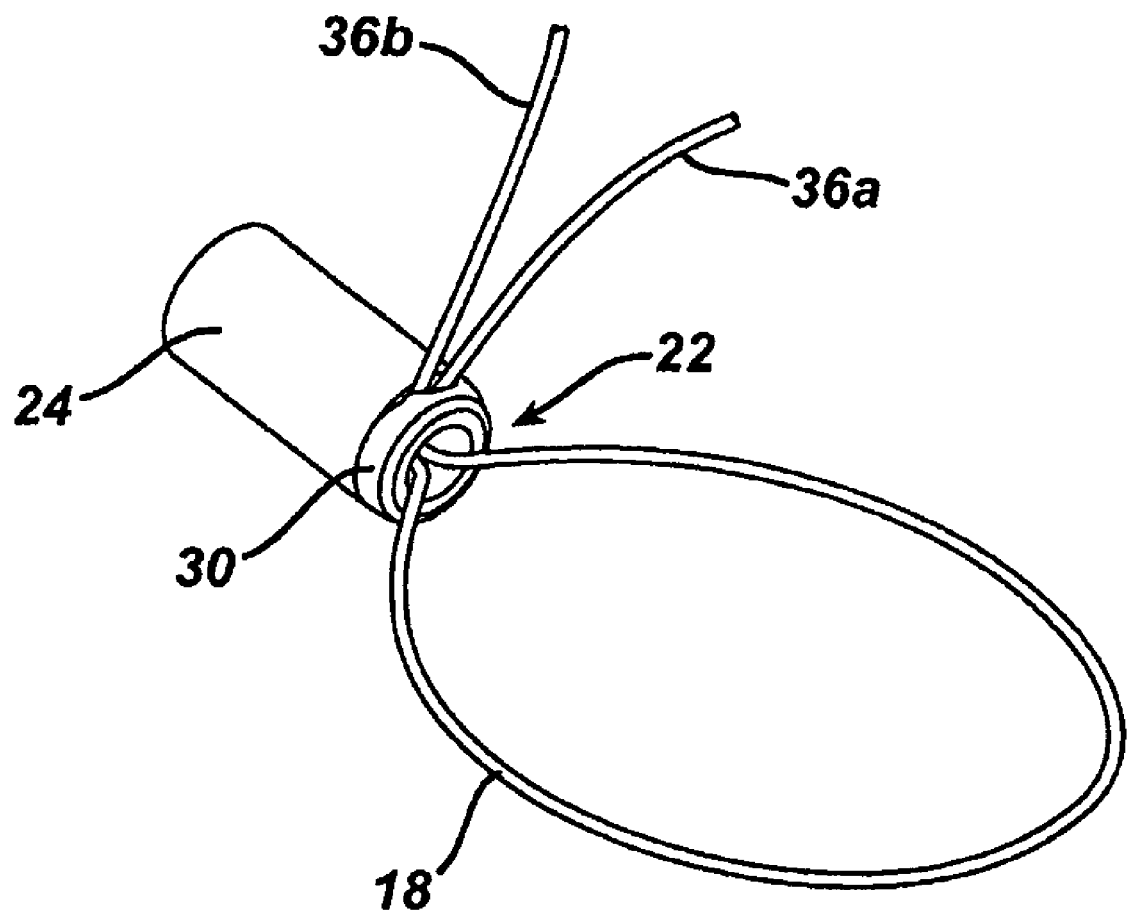
FIG. 2 is a perspective view of the knotting element of FIG. 1A with the knotting element in a locked configuration.

Many configurations for a knotting element are possible, and one exemplary knotting element 14 is shown in more detail in FIGS. 1A-2. As noted above, the knotting element 14 can generally include the inner member 22 and the outer member 24 that is slidable over the inner member 22. Although, the two members 22, 24 can have any shape or configuration known in the art, in one embodiment, the two members 22, 24 can be generally cylindrical or tubular in shape, and the outer member 24 can be positionable concentrically around the inner member 22. The inner member 22 can have a flange 30 extending radially outward from its distal-most end. The flange 30 can generally have an outer diameter that is larger than an inner diameter of the lumen in the outer member 24, and it can have an opening 28 that opens into an axially extending channel or bore 29 through the inner member 22. A proximal facing surface 32 of the flange 30 can be configured to abut a distal-most end 34 of the outer member 24, as shown in FIG. 2, to prevent the outer member 24 from sliding further distally over the inner member 22.

In one embodiment, the knotting element 14 can be configured to be movable between two configurations, for example, an open or delivery configuration and a deployed or locked configuration. In the open configuration, the outer member 24 is positioned proximally to the inner member 22, as shown in FIGS. 1A-1C and suture is free to slidably move therethrough. The strand of suture 26 can be folded to form a loop at one end that extends distally from the bore 29 in the inner member, and two free ends at the other end of the folded suture that extend proximally from the delivery device. The suture can extend from the inner member 22 out through a window 38 formed in the extension portion 40. The window 38 can be accessible between the inner and outer members 22, 24. The strand of suture 26 can then travel along the outside of the outer member 24, along a portion of the outer shaft, and then it can re-enter and extend through a slot 37 in the actuator shaft 15 at a location proximal to the distal end and it can travel to the proximal end of the device 10.

As will be appreciated by those skilled in the art, any method of forming a loop of suture within the knotting element 14 can be used. For example, the strand of suture 26 can enter and leave the extension portion 40 through different windows. In the deployed or locked configuration, the outer member 24 can be positioned circumferentially around the inner member 22 to engage and lock the strand of suture 26 therebetween. In particular, the portion of suture extending out from window 38 will be engaged between the outer surface of the inner member 22 and the inner surface of the outer member 24. Surface features, such as a plurality of spaced ridges 42, can be formed in a sidewall of the inner member 22 to grip and hold the strand of suture 26 as the outer member 24 is moved over the inner member 22. As will be appreciated by those skilled in the art, any surface features capable of providing a frictional or gripping surface can be formed in the surface of the inner member 22. In the locked configuration, the suture is no longer freely slidable through the knotting element 14 and the size and tightness of the loop of suture 18 is locked, as shown in FIG. 2 and as will be described in more detail below.

In the open configuration, opposing end portions 36a, 36b of the strand of suture 26 can be manipulated to change the size of the loop 18. For example, one or both of the opposing end portions 36a, 36b can be pulled to form a tighter loop 18 extending from the inner member 22. Alternatively, one or both of the opposing end portions 36a, 36b can be pushed through the bore 29 to increase the size of the loop 18. This manipulation can be done repeatedly as needed to attain a desired loop size both before the deployment device 12 is inserted into a body and/or after the deployment device 12 is inserted into the body and is near tissue. This is particularly advantageous in that the deployment device 12 does not have to be withdrawn from a body during surgery in order to reset or enlarge the size of the loop 18. Increasing the loop size can be accomplished simply by manipulation of the suture end portions 36a, 36b, which preferably extend out of the proximal end of the device and outside of the body. In addition, the loop of suture 18 can be bendable with respect to the knotting element 14. For example, the loop of suture 18 can be bent out of its original, flattened delivery plane into an orientation that is more suitable for receiving tissue. In some embodiments, the loop of suture 18 can be bent to any angular orientation as needed with respect to the knotting element to receive tissue therein. A person skilled in the art will appreciate the variety of ways and situations in which the loop of suture can be bent, sized, changed and manipulated.

In the locked configuration, the outer member 24 can move or slide distally over the inner member 22 until the distal end 34 of the outer member 24 contacts the proximal surface 32 of the flange 30. As the outer member 24 moves over the inner member 22, the strand of suture 26 exiting the inner member 22 in a proximal direction is moved or bent distally. In the locked configuration, the suture 26 is locked between the surface of the inner member 22 and the outer member 24 as the suture is pressed into the ridges 42 in the surface of the inner member 22. The suture 26 extends out between the distal end 34 of the outer member 24 and the proximal surface 32 of the flange 30, as shown is FIG. 2. In this way, the loop of suture 18 can be locked around tissue.

Figure 5A:
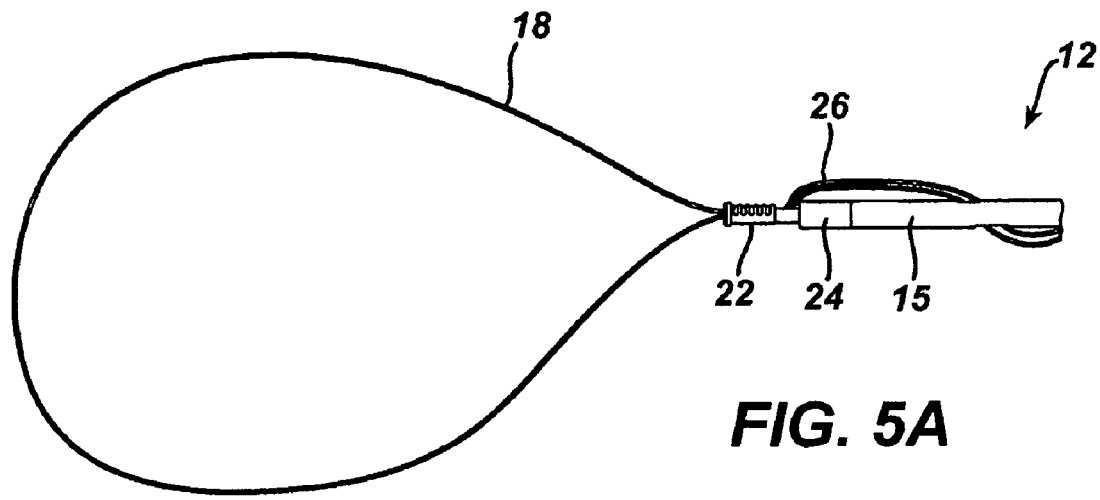
FIG. 5A is a side view of a knotting element with a loop extending along an axis of a delivery device.
Figure 5B:
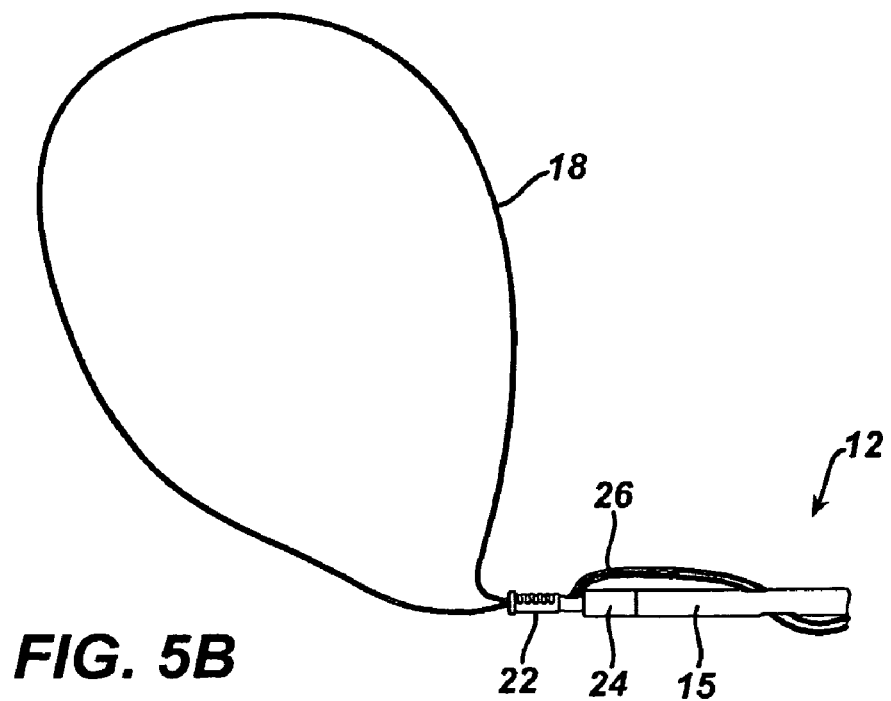
FIG. 5B is a side view of the knotting element of FIG. 5A with a loop bent at an angle relative to the axis of the delivery device.

Any type of suture can be used to form the loop of suture 18, regardless of material, stiffness, diameter, and/or other characteristics. Various sized knotting elements can be used and thus suture strands with various diameters can be used to complement a particular sized knotting element and/or a particular procedure. In general, the suture can be flexible to allow it to be threaded, manipulated, and bent as needed. In addition, the suture can have a stiffness that allows it to retain a certain configuration once moved into that configuration. For example, the suture can be formed from a deformable wire and it can be bent out of one plane and into another plane to better receive tissue, as shown in FIGS. 5A and 5B, the suture can maintain its adjusted orientation. In addition, the stiffness of the suture can be such that it can be pushed through the knotting element to adjust and/or enlarge a size of the loop of suture without collapsing the strand. The suture can also be biocompatible and/or bioresorbable, and can be formed of any material in the art including, but not limited to, surgical gut, Dexon® (polyglycolic acid), chromic suture materials having absorption times of between about 10 days and 40 days, nylon (Ethilon®), prolene, and/or braided materials including cotton, silk, nylon, and multifilament Dacron®.

Figure 3A:
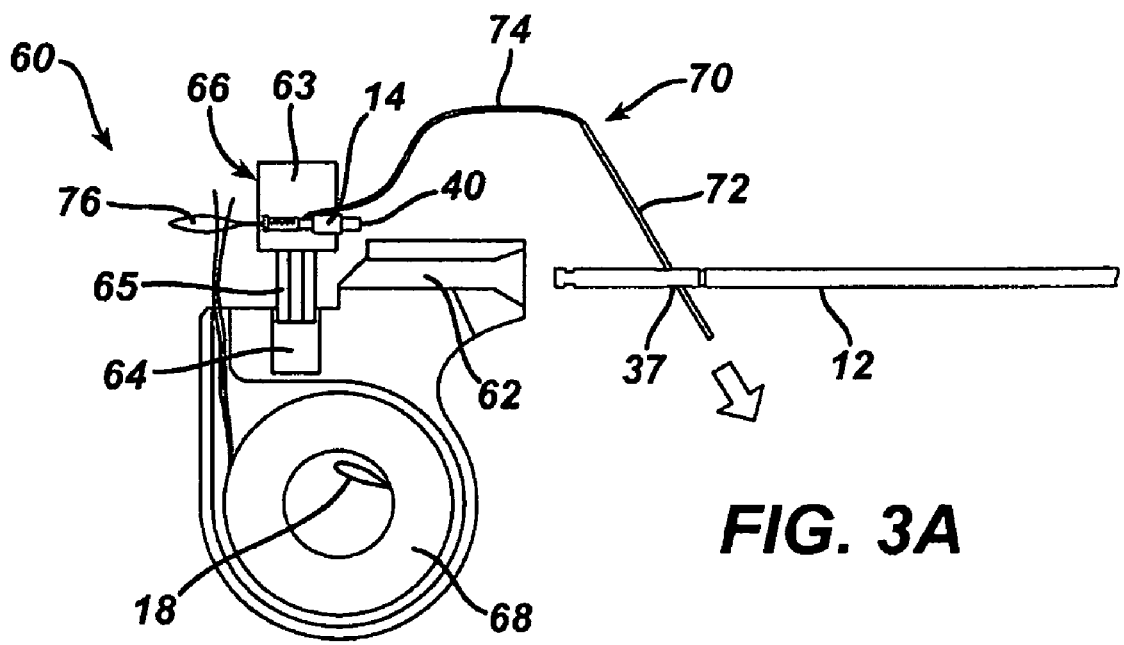
FIG. 3A is a cross-sectional view of one embodiment of a loading device having a suture loading portion and a knot loading portion.
Figure 3B:
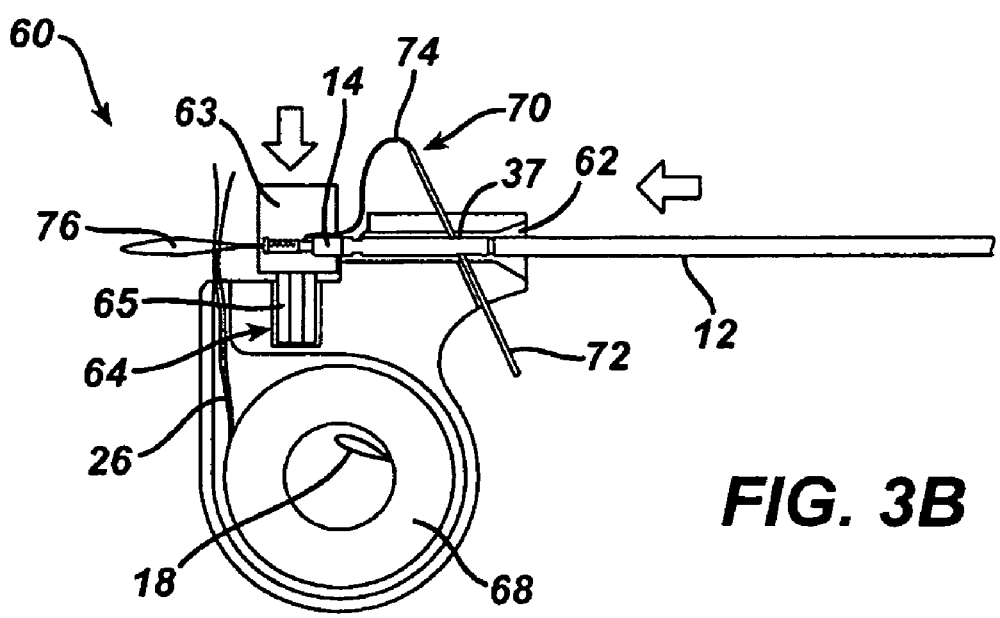
FIG. 3B is a cross-sectional view of the loading device of FIG. 3A illustrating insertion of a deployment device into the loading device and loading of a knotting element.

Devices and methods for threading the knotting element 14 and for loading the deployment device 12 with the knotting element 14 and the preloaded loop of suture 18 are also provided. A loading device can generally include a suture loading portion for loading a loop of suture into a knotting element, and/or a knot loading portion for loading a knotting element onto a delivery device. In one embodiment, an example of which is shown in FIGS. 3A-3C, a loading device 60 is provided that can facilitate loading the knotting element 14 onto the deployment device 12 and threading the loop of suture 18 into the knotting element 14 such that the deployment device 12 is configured for insertion into a body, as shown in FIG. 3D, to ligate and/or secure tissue. In the illustrated embodiment, the loading device 60 includes a loading port channel 62 for receiving a distal portion of the deployment device 12 for loading the knotting element 14 thereon, a cartridge port 64 for receiving a knotting element cartridge 66, and a suture spool 68 for loading the loop of suture 18 into the knotting element 14.

The knotting element cartridge 66 can have various configurations, but in the illustrated embodiment, the cartridge 66 includes a housing 63 for holding and/or containing the knotting element 14 to be loaded into the deployment device 12, and an insertion tab 65 that can be inserted into the cartridge port 64. A suture threading mechanism 70 can also be associated with the cartridge 66 to assist the threading of the suture into the knotting element 14 from the suture spool 68 as will be described in detail below. In one embodiment, to load the knotting element 14 onto the deployment device 12, the insertion tab 65 of the cartridge 66 can be inserted into the cartridge port 64, thereby axially aligning the extension portion 40 of the inner member 22 with the loading port channel 62. The deployment device 12 can be inserted into the loading port channel 62, as shown in FIG. 3B, such that the distal end of the actuator shaft 15 receives and secures the aligned extension portion 40 of the knotting element 14. As described above, the extension portion 40 is an extension of the inner member 22 and separated from the inner member 22 by a frangible portion such that the knotting element 14 can later be deployed from the deployment device 12 by breaking the frangible portion.

While there are various ways to thread the knotting element 14, in the illustrated embodiment, the suture threading mechanism 70 can be preloaded within the knotting element 14 positioned within the cartridge 66 and it can include a suture threading needle 72 and a flexible threader 74. The flexible threader 74 can be any flexible strand of material, such as a strand of suture, plastic, and/or flexible wire, and it can extend from the needle 72, through the knotting element 14, and out the distal end to form a grasping loop 76 designed to provide a threading eye for the strand of suture 26. The suture threading needle 72 can be inserted through the slot 37 of the deployment device 12 in a configuration that allows the suture threading needle 72 to be pulled through the slot 37 and to thereby thread the flexible threader 74 and the strand of suture 26 through the knotting element 14 and the slot 37.

In use, the strand of suture 26 is pre-wound on the suture spool 68, terminating in the loop of suture 18. The terminal free ends of the strand of suture 26 can be threaded through the grasping loop 76. The suture threading needle 72 can be pulled through the slot 37 of the deployment device 12 to pull the strand of suture 26, held by the grasping loop 76, through the knotting element 14 and through the slot 37 of the deployment device 12. In this way, the strand of suture 26 is unwound from the suture spool 68 until the loop of suture 18 is positioned within and extends from the distal end of the knotting element 14. The deployment device 12 can be removed from the loading port channel 62 with the knotting element 14 and the loop of suture 18 now configured to be inserted into a body to ligate and secure tissue, as shown in FIG. 3D.

In use, the deployment device 12 can generally be inserted into a patient's body to deploy the preloaded loop of suture 18 to ligate tissue. In further preparation for insertion of the deployment device 12 into a patient's body, the delivery sheath 16 can be slidably moved to surround and cover at least the loop of suture 18 and can optionally cover the knotting element 14 and one or more portions of the deployment device 12. In this way, the loop of suture 18 is protected from snagging or catching during insertion through a patient's body to the necessary tissue ligation location. The deployment device 12 can now be inserted into a patient's body using any methods known in the art, as noted above, and can be placed in proximity to tissue to be ligated. For example, the deployment device 12 can be inserted through any working channel created for a surgical procedure, such as a working channel of a minimally invasive device. The working channel can be positioned anywhere within a patient's body as needed for a specific procedure, for example, in an anterior portion of a stomach for transgastric access and/or vaginally for transvaginal access. Once the deployment device 12 is inserted through such a working channel and maneuvered to a desired location, the delivery sheath 16 can be slidably retracted from around the loop of suture 18 and optionally the knotting element 14 so that the same is ready for manipulation and deployment when required.

FIGS. 4A-4B illustrate an exemplary method for ligation of tissue 100 once the deployment device 12 has been inserted to the required location. As shown, a grasping device 102 can be used to hold or grasp a portion of the tissue 100 to maneuver and manipulate the tissue 100 through the loop of suture 18. Alternatively, the loop of suture 18 can simply be maneuvered and placed around tissue to be ligated without the use of a grasping tool. Using opposing end portions 36a, 36b of the strand of suture 26, the size of the loop of suture 18 can be increased or decreased as needed to accommodate the required size of the tissue 100 to be ligated. In addition, the loop of suture 18 can be bent out of its original insertion plane, e.g., by twisting, bending, and/or turning the loop of suture 18, as shown for example in FIGS. 5A and 5B, to any angular orientation with respect to the knotting element 14 to be better oriented to be positioned around tissue.

Once the loop of suture 18 is positioned around the tissue, the size of the loop of suture 18 can be decreased until the tissue is ligated as needed by pulling proximal ends of the suture strand proximally and/or pushing the knotting element 14 distally toward the tissue 100. A trigger mechanism or activation mechanism can be activated to cause the actuator shaft 15 to move relative to the inner shaft (not shown) to thereby move the outer member 24 over the inner member 22. Once the knotting element 14 is locked such that the outer member 24 is enclosing the inner member 22 with the strand of suture 26 secured therebetween, further distal movement of the actuator shaft 15 is resisted due to the outer member 24 being flush against the flange 32 of the inner member 22. Thus, further distal movement of the actuator shaft 15 is effective to snap or break the frangible portion on the extension portion 40 of the inner member 22, thereby deploying the knotting element 14 from the deployment device 12.

The knotting element 14 remains in the locked configuration as it engages the suture such that the loop of suture 18 remains secured about the tissue 100. The deployment device 12 can be withdrawn from the location and can be reloaded and reused as needed for a particular procedure. In this way, suturing devices and methods are provided that are capable of delivering a preloaded loop of suture to a surgical site that is ready to be deployed to ligate tissue without any need for threading or knotting by the surgeon during the surgical procedure. A person skilled in the art will appreciate that a variety of other techniques and methods can be used to insert and deploy the knotting element within a patient and that any described herein are exemplary in nature.

In other embodiments, a kit can be provided that can include the delivery device 10 and the loading device 60. More particularly, the kit can include the deployment device 12, the knotting element 14, the loop of suture 18, the delivery sheath 16, and the loading device 60. In all embodiments, a plurality of knotting elements and strands of suture can be provided so that the deployment device 12 can be reloaded as many times as needed during a particular procedure.

The various devices disclosed herein, or portions thereof, can be designed to be disposed of after a single use, or they can be designed to be used multiple times. For example, after at least one use, the device can be disassembled, followed by cleaning or replacement of particular pieces, and subsequent reassembled. Replacement of pieces can also include replacement of portions of particular elements. Upon cleaning and/or replacement of particular parts, the device can be reassembled for subsequent use either at a reconditioning facility, or by a surgical team immediately prior to a surgical procedure. Those skilled in the art will appreciate that reconditioning can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A tissue ligation system, comprising: a deployment device having a knotting element coupled thereto, the knotting element having an outer member and an inner member that is slidably received in the outer member; a strand of suture passing thought a lumen in the inner member, the suture forming a loop extending distally from the inner member and having trailing ends extending proximally from the inner member; a handle coupled to a proximal end of the deployment device and having an actuation mechanism disposed thereon; and a sheath slidably disposed over the deployment device, the knotting element, and the loop, the sheath being operably coupled to the actuation mechanism such that the movement of the actuation mechanism is effective to slide the sheath over the deployment device, the knotting element, and the loop; wherein when the outer member is positioned over the inner member, the strand of suture is engaged therebetween with trailing ends of the suture extending distally from the knotting element in the same direction as the loop.

2. The system of claim 1, wherein the loop extends from a distal end of the knotting element and the deployment device is coupled to a proximal end of the knotting element.

3. The system of claim 1, wherein a size of the loop extending from the knotting element is adjustable relative to the knotting element.

4. The system of claim 3, wherein the size of the loop extending from the knotting element is increasable.

5. The system of claim 1, wherein the loop is configured to be placed around tissue and tightened to ligate tissue.

6. The system of claim 1, wherein the loop is bendable out of a plane containing the loop to reorient the loop to better receive tissue therethrough.

7. The system of claim 1, wherein the inner and outer members are substantially concentric such that when the outer member is positioned over the inner member, the trailing ends of the strand of suture are gripped therebetween.

8. The system of claim 1, wherein the deployment device is configured to advance the outer member over the inner member to move the knotting element to a locked position where a size of the loop is fixed.

9. The system of claim 8, wherein the inner member includes a flange positioned on its distal end for limiting distal movement of the outer member over the inner member.

10. The system of claim 1, wherein the sheath is configured to protect the loop of suture during delivery through tissue.

11. The system of claim 1, wherein the sheath is retractable from around the loop of suture.

12. The system of claim 1, wherein an outer surface of the inner member includes a plurality of surface features for engaging the suture.

13. A method for deploying a suture locking device, comprising: positioning a knotting element and a loop of suture extending from the knotting element within a sheath of a delivery device, the knotting element having an inner member and an outer member; inserting the delivery device through tissue in a body; engaging an actuation mechanism disposed on a proximal end of the delivery device and positioned outside of the body to retract the delivery sheath from around the loop of suture; and advancing the outer member over the inner member such that a portion of the suture that extends proximally from a lumen formed in the inner member is moved distally along an outer surface of the inner member.

14. The method of claim 13, further comprising, prior to advancing, positioning the loop of suture around tissue to be ligated.

15. The method of claim 14, wherein positioning the loop of suture comprises manipulating the loop of suture to position the loop of suture around tissue.

16. The method of claim 14, wherein positioning the loop of suture comprises pulling tissue to be ligated through the loop of suture.

17. The method of claim 14, further comprising activating a deployment device to advance the outer member over the inner member to engage the suture therebetween.

18. The method of claim 17, further comprising, prior to activating, advancing the knotting element along the suture to engage the tissue with the loop of suture.

19. The method of claim 18, further comprising releasing the knotting element from the deployment device and reloading a second knotting element with a suture loop extending therefrom onto the deployment device using the loading device.

20. The method of claim 13, wherein positioning the knotting element comprises advancing the delivery sheath over a deployment device having the knotting element coupled to a distal end thereof.

21. The method of claim 20, further comprising, prior to positioning, threading the suture through the knotting element and loading the knotting element onto the deployment device using a loading device.

22. The method of claim 13, further comprising increasing a size of the loop of suture.

23. The method of claim 13, further comprising bending the loop of suture out of a plane containing the loop of suture to better orient the loop of suture to receive tissue therethrough.

24. The method of claim 13, wherein the delivery sheath is inserted through a working channel of a minimally invasive device.

25. A loading device, comprising:
a housing having:
a strand of suture wound about a suture spool and terminating in a loop;
a port configured to receive a cartridge; and
a channel configured to receive a distal portion of a delivery device; and
a cartridge having a knotting element disposed therein and configured such that when the cartridge is positioned in the port, the knotting element is longitudinally aligned with the channel to allow the delivery device to mate to the knotting element.

26. The device of claim 25, wherein a longitudinal axis of the port is substantially perpendicular to a longitudinal axis of the channel.

27. A kit, comprising:
a loading device having a knotting element disposed therein and a strand of suture disposed therein configured to be threaded through the knotting element; and
a delivery device configured to receive the knotting element with suture threaded therethrough, the strand of suture forming a loop extending distally from the knotting element and having trailing ends extending proximally from the knotting element, and to deliver the knotting element and suture through tissue;
wherein the knotting element includes an inner member slidably coupled to an outer member and the delivery device is configured to slide the outer member relative to the inner member, thereby folding the trailing ends of the suture over an outer surface of the inner member.

28. The kit of claim 27, wherein the delivery device includes a deployment device for deploying the knotting element to engage the suture, and a sheath disposed over the deployment device.

* * * * *